United States Patent [19]
Vanreusel et al.

[11] 3,972,719
[45] Aug. 3, 1976

[54] PHOTOGRAPHIC DEVELOPER COMPOSITIONS

[75] Inventors: Gerard Laurens Vanreusel, Hove; Raoul Jan Bortels, Wilrijk, both of Belgium

[73] Assignee: AGFA-GEVAERT N.V., Mortsel, Belgium

[22] Filed: July 14, 1975

[21] Appl. No.: 595,442

Related U.S. Application Data

[63] Continuation-in-part of Ser. No. 426,134, Dec. 19, 1973, abandoned, which is a continuation of Ser. No. 226,232, Feb. 14, 1972, abandoned.

[30] Foreign Application Priority Data

Feb. 15, 1971 United Kingdom................ 4646/71
Jan. 11, 1972 United Kingdom................ 1282/72

[52] U.S. Cl.................... 96/66.3; 96/66.4; 96/66.5
[51] Int. Cl.².......................... G03C 5/30
[58] Field of Search.............. 96/66 R, 66.3, 66.4, 96/66.5

[56] References Cited
UNITED STATES PATENTS

| | | | |
|---|---|---|---|
| 3,128,180 | 4/1964 | Henn et al. | 96/66.4 |
| 3,129,097 | 4/1964 | van Hoof et al. | 96/66.3 |
| 3,158,483 | 11/1964 | Lowe et al. | 96/66.3 |
| 3,490,905 | 1/1970 | Blake | 96/63 |
| 3,490,906 | 1/1970 | Blake | 96/63 |
| 3,532,499 | 10/1970 | Willems et al. | 96/66.3 |
| 3,573,914 | 4/1971 | Masseth | 96/66.4 |
| 3,615,488 | 10/1971 | Drago et al. | 96/66 |

*Primary Examiner*—Mary F. Kelley
*Attorney, Agent, or Firm*—William J. Daniel

[57] ABSTRACT

This invention relates to the addition of a nitroindazole and a polymer containing a plurality of alkylene oxide units and having a molecular weight of at least about 1500, to an aqueous lithographic developer system.

15 Claims, No Drawings

PHOTOGRAPHIC DEVELOPER COMPOSITIONS

CROSS REFERENCES TO RELATED APPLICATION

This application is a continuation-in-part of Ser. No. 462,134, filed Dec. 19, 1973, now abandoned, which is a continuation of Ser. No. 226,232 filed Feb. 14, 1972, now abandoned.

This invention relates to a photographic developer composition suited for use in the development of photographic silver halide recording materials and to a developing process suited for producing half-tone images.

In the reproduction of continuous tone material for mechanical printing purposes, it is customary to make a half-tone photographic intermediate, usually a film negative, in which the gradations in tone are represented by dots of differing size. The quality of the resulting half-tone picture is closely connected with the shape, spectral density, and uniformity of the dots of the half-tone print.

In the production of half-tone prints having a dot quality (high contrast and sharpness) characteristic for images showing a so-called "lith-gradation" up till now developers essentially consisting of hydroquinone, alkali, an alkaline metal bromide, and a relatively small amount of sulphite ions have been used. The term "lith gradation" is defined by Ewald Fred Noemer in the Handbook of Modern Halftone Photography, Perfect-Graphic Arts Supply Company P.O. Box 62 Demarest, N.J. 07627 (1965) p. 55. Hydroquinone developers having a low sulphite ion concentration are commonly referred to as "lith-type developers" and their mechanism of operation is described by J.A.C. Yule in the Journal of the Franklin Institute, 239 (1945), pages 221 to 230.

The properties of lith-type developers are believed to result from autocatalytic action, often called "infectious development", due to a local high concentration of the oxidation products of the developing agent, which can build up as a result of the low sulphite ion concentration. Therefore, the sulphite ion concentration has to be kept at a low level to maintain the lith-type development characteristic. This is achieved in all known commercial developers of this type by the use of the addition product of formaldehyde and sodium hydrogen sulphite, the so-called sodium formaldehyde hydrogen sulphite, which acts as a sulphite ion buffer.

It has to be noticed that before use such developer solutions have to be stored in two parts, since the sodium formaldehyde hydrogen sulphite in the alkaline medium of the developer dissociates to form the sulphite ion improving the keepability but also an equimolar amount of formaldehyde that reacts with hydroquinone and destroys its developing power.

Another point to be noticed is the fact, that when used in continuous transport processing machines the commonly known lith-type developers for high-contrast films give rise to results of inferior quality as compared with carefully effected tray processing. In machine processing drag streaks are produced as a result of locally varying concentration of the developing agent and its exhaustion products.

These drag streaks occur in areas of high development, i.e. the areas with a relatively high dot concentration (50-90% of the area is occupied by dots), which are adjacent to areas of low development (only 20% of the area or less is occupied by the dots). The developer that is "dragged in" from the area of high development contains less developing agent and more development reaction products (bromide ions) than the developer that is present in the low development area. The dots in a high-contrast film are locally distorted thereby and they exhibit changes of size depending on the orientation and direction of travel through the machine processor. This dot distortion is a manifestation of discontinuities or plateaus in the H & D curve of high-contrast films processed in continuous transport processing machines in which the film is transported by means of rollers.

It would therefore be very desirable to have a stable unitary developer solution suited for use in the reproduction of halftones, that when used in a continuous transport processing machine produces screen images with dots of very high density that show practically no halation and that do not suffer from drag streaks and dot distortions.

In accordance with the invention described in the U.S. Pat. No. 3,675,488 there is provided a high-contrast unitary processing solution which contains a dihydroxy benzene developing agent, a monoaldehyde bisulfite and cysteine which works synergistically with the aldehyde to produce desired effects of increased developer lift time and image sharpness. In a preferred embodiment of said invention the developer contains as organic antifoggant a nitrobenzimidazole or nitroindazole.

According to the U.S. Pat. No. 3,573,914 a unitary lithographic developer is provided which contains a special condensation product of a formaldehyde bisulfite compound with an amino compound and a 5- or 6-nitro-indazole which is added to reduce drag streaks in continuous processing.

There has now been found that a silver halide recording material in which the halide consists of at least about 50 mole % of chloride and which has been subjected to an exposure for producing a halftone print yields a halftone print with sharp non-distorted dots by development with a high free sulfite containing unitary aqueous alkaline developer having excellent keeping properties and containing:

1. a p-hydroxybenzene developing agent in an amount of about 0.05-0.50 mole per liter,
2. a sulfite compound providing an amount of free sulfite ions ($SO_3^{--}$) of at least about 5 grams per liter,
3. a sufficient amount of an alkaline compound to impart to said composition a pH of about 9.7–11.5,
4. a nitro-indazole corresponding to the following general formula:

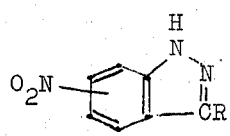

wherein:
R is hydrogen or a lower ($C_1$-$C_5$) alkyl group, and the nitro-group is in the 5- or 6-position,
5. a polymer containing a plurality of alkylene oxide units and having a molecular weight of at least about 1500, said polymer being present in a concentration of at least 500 mg per liter, and 6. bromide ions in a concentration of at least 0.2 g per liter, said composition containing not more than about 0.05 g/l of any auxiliary developing agent that shows a superadditive developing effect with said p-dihydroxybenzene developing agent.
benzene developing agent.

Unlike the developer composition of the U.S. Pat. No. 3,615,488 the developer composition of the present invention needs not to be bromide free for obtaining particularly high dot quality.

The present developer composition differs considerably from the developer composition of the U.S. Pat. No. 3,573,914 in that it does not contain a carbonyl sulfite amine to provide a low level of sulfite ion. In spite of high free sulfite concentration the present developer is capable of yielding images showing the lith-gradation and halftone images of high dot quality.

It has been established experimentally that the particularly high dot sharpness under the conditions of said high free sulfite ion content is due to a synergistic effect of the nitro-indazole and the polymer containing a plurality of alkylene oxide units.

The polyoxyalkylene compound or a mixture of polyoxyalkylene compounds is present in the developer preferably in the range of about 0.5 g to 2.0 g per liter of developer composition but the said compound or mixture of compounds may also be present in the photographic material.

A preferred polyoxyalkylene compound for use in the present developer composition is a polyoxyethylene glycol with an average molecular weight of at least 1500. A particular useful polyoxyethylene compound is e.g. the condensation product prepared as described in preparation 2 of British Patent Specification 945,340.

Other polymeric oxyalkylene compounds that may be applied in the developer composition of the present invention are described in the United Kingdom Patent Specifications 600,058 filed Jan. 10, 1946 by E.I. du Pont de Nemours, 871,801 filed Nov. 30, 1956 by Kodak, 920,637 filed May 7, 1959, 940,051 filed Nov. 1, 1961, 949,643 filed Nov. 2, 1961, all three by Gevaert Photo-Producten N.V., 991,608 filed June 14, 1961 by Kodak, 1,015,023 filed Dec. 24, 1962, 1,091,705 filed May 20, 1965, both by Gevaert Photo-Producten N.V., 1,107,022 filed Oct. 7, 1965, 1,147,817 filed Aug. 19, 1966, 1,162,135 filed Oct. 11, 1965 and 1,184,434 filed Aug. 30, 1966 all four by Gevaert-Agfa N.V., in the published German Patent Applications 1,141,531 filed Jan. 24, 1962 by Perutz Photowerke G.m.b.H., 1,188,439 filed May 16, 1964 by Fuji Shashin Film Kabushiki Kaisha, and in the U.S. Pat. Nos. 1,970,578 of Conrad Schoeller and Max Wittwer, issued Aug. 21, 1934, 2,240,472 of Donald R. Swan, issued Apr. 29, 1941, 2,423,549 of Ralph K. Blake, William Alexander Stanton, Ferdinand Schulze, issued July 8, 1947, 2,441,389 of Ralph K. Blake, issued May 11, 1948.

In the developing process of the present invention the nitro-indazole is present in the developing liquid at least during the stage of the development in such a concentration that an image having the lith-gradation under the specified conditions of high sulphite concentration is still obtained.

A developer composition containing said high sulphite ion concentration in the absence of the nitro-indazole does not show any noticeable lith-gradation anymore since as is known the oxidation products (semiquinones) of the developing agent so quickly react with the sulphite ions that they cannot act as development accelerator.

An explanation for the phenomenon that the lith-gradation is obtained in the presence of the nitro-indazoles under the development conditions of high sulphite ion concentration cannot be given at the present stage of research. It has been assumed that the nitro-indazoles prevent the interaction of the sulphite ions with the oxidation products of the developer.

Nitro compounds that are particularly suited for use according to the present invention correspond to one of the following structural formulae:

A.

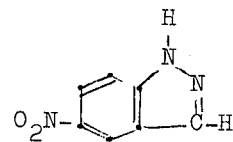

(5-nitro-indazole)

This product is prepared as follows: 2 parts by weight of 5-nitro-2-amino-toluene dissolved in 100 parts of acetic acid are treated at 25°C with a concentrated aqueous solution containing 0.91 part by weight of sodium nitrite. The resulting solution is allowed to stand for a day and is then concentrated nearly to dryness. The residue is washed well with water to remove the remaining acetic acid. The product is obtained in pure form by recrystallization from dilute methanol.
Melting point: 206°–208°C.

B.

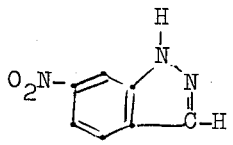

(6-nitro-indazole)

(Preparation: Beilstein Vol. XXIII E II page 146, melting point: 181°C decomp.)

C.

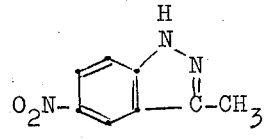

(3-methyl-5-nitro-indazole)

This product is prepared as follows:
A solution of 11.4 g (0.05 mole) of mercaptobutane sulphonic acid guanidine salt and 5.3 g (0.05 mole) of sodium carbonate in 100 ml of water is added to a solution of 10.5 g (0.05 mole) of 2-chloromethyl-5-nitrobenzimidazole in 425 ml of methanol and 100 ml of water. The reaction mixture is stirred for 4 hours at room temperature, refluxed for 1 hour, and then filtered. The resulting solution is conducted over an ion exchanger and the element is evaporated completely by evaporation. The residue is recrystallized from 40 ml of water, cooled down, and filtered with suction. The solid product is dried under reduced pressure of 15 mm Hg at 100°C.
Yield: 11.2 g.

The concentration of the nitro-indazole compound(s) used according to the present invention preferably varies between 5 and 100 milligram per liter of developer solution.

According to a particularly preferred embodiment an aqueous alkaline developer composition is used that has a pH between 9.7 and 11.5 and contains 5-nitroindazole in an amount of 10 to 30 mg per liter.

The developing agents that can be employed in the developer composition of the present invention can be any of these suitable for the production of high contrast images of the class of p-dihydroxybenzene developing agents.

A preferred developing agent is hydroquinone.

Suitable developing agents derived from hydroquinone are:
chlorohydroquinone,
bromohydroquinone,
isopropylhydroquinone,
toluhydroquinone,
methylhydroquinone,
2,3-dichlorohydroquinone,
2,5-dimethylhydroquinone,
2,3-dibromohydroquinone,
1,4-dihydroxy-2-acetophenone-2,5-dimethylhydroquinone,
2,5-diethylhydroquinone,
2,5-di-p-phenethylhydroquinone,
2,5-dibenzoylaminohydroquinone,
2,5-diacetaminohydroquinone, etc.

Esters of such compounds, e.g., formates and acetates can likewise be applied. These developing agents can be used along or in admixture with each other in any concentration that is effective for the desired development.

A preferred concentration of p-dihydroxybenzene developing agent as sole developing agent is in the range of about 0.10 to about 0.30 mole per liter.

Nevertheless, minor amounts of auxiliary developing substances may be present with the proviso that they do not substantially affect the high contrast results (gamma > 15) aimed at.

When an auxiliary developing agent or mixture of such agents that in combination with said p-dihydroxybenzene developing agent shows a superadditive developing effect is used as is known e.g. for hydroquinone and monomethyl-p-aminophenol type developers or hydroquinone-1-phenyl-3-pyrazolidinone type developers the auxiliary development agent must not be present in amounts destroying the lith gradation. When stating that the developer composition is substantially free from any auxiliary developing agent that shows a superadditive developing effect with said p-dihydroxybenzene developing agent, we mean that the developer composition does not contain more than 0.05 g per liter of the superadditively working auxiliary developing agent(s).

Ascorbic acid not acting as superadditively working auxiliary developing agent may be used in the developer composition of the present invention as a preservative e.g. in a concentration up to 3 g per liter.

Preferably the sulphite ions are incorporated into the developer composition e.g. starting from an alkaline metal hydrogen bisulphite or metabisulphite or a corresponding ammonium salt. In addition to the relatively high amount of free sulphite ions (more than 5 g per liter) the developer may contain an amount of masked sulphite ions in the form of a carbonyl hydrogen sulphite addition product e.g. sodium formaldehyde hydrogen sulphite.

When a lith type developer containing said addition product in the presence of said nitro-indazole(s) and polyoxyalkylene polymer(s) is used no substantial reduction in dot quality of a screen image is obtained by freeing more sulphite ions on raising the pH. An increase of pH improves the development speed as is commonly known.

The concentration of free sulphite ion is preferably in the range of 5 to 100 grams per liter.

The developer composition according to the present invention may contain compounds known to increase the development speed e.g. onium and polyonium compounds, preferably of the ammonium, phosphonium, and sulphonium type or mixtures thereof. Specific onium and polyonium compounds for accelerating the development are e.g. trialkylsulphonium salts such as dimethyl-n-nonyl-sulphonium p-toluene sulphonate, tetraalkyl-ammonium salts such as dodecyltrimethylammonium p-toluene sulphonate, alkylpyridinium, and alkylquinolinium salts such as 1-m-nitrobenzylquinolinium chloride and 1-dodecylpyridinium chloride, alkylene-bis-pyridinium salts such as N,N'-tetramethylene-bispyridinium chloride, quaternary ammonium and phosphonium polyoxyalkylene salts especially polyoxyalkylene-bis-pyridinium salts, examples of which can be found in the United States Patent Specification 2,944,900 of Burt H. Carroll, Herbert S. Elins, James L. Graham and Charles V. Wilson, issued July 12, 1960, etc.

As compound accelerating the developing speed a polyoxyethylene-bispyridinium salt e.g. 1,1'-[ethylene-tris(oxyethylene)]bis-(pyridinium p-tolusulphonate) is used preferably. A suitable concentration of said polyoxyethylene-bis-pyridinium salt is in the range of about 0.1 to 3.0 grams per liter of developer composition.

The developer composition according to the present invention contains free bromide ions in a concentration preferably in the range of about 0.2 to about 5.0 g per liter developer solution.

Developer solutions according to the present invention can be left in the machine processor for several weeks without marked degradation, whereas prior art developers must be kept in the form of two stock solutions to be mixed just prior to use.

Preferred high-contrast photographic elements for processing with a developing composition according to the present invention contain a silver halide emulsion layer, in which the halide comprises at least 50 mole % of chloride. Preferably the silver halide emulsion comprises at least 70 mole % of chloride, the balance, if any, being bromide. Such preferred emulsions provide particularly good results in eliminating drag streaks and dot distortions. The silver halide emulsion may also contain a small amount of iodide, e.g. less than 5 mole %, if desired. Likewise quite useful are silver halide emulsions comprising 100 mole % of chloride.

A silver halide emulsion layer suitable for processing according to the present invention may contain any of hydrophilic water-permeable binding materials suitable for this purpose. Suitable materials include gelatin, colloidal albumin, polyvinyl compounds, cellulose derivatives, acrylamide polymers etc. Mixtures of these binding agents may be used. The binding agents for the emulsion layer of the high contrast photographic element may also contain dispersed polymerized vinyl compounds. Such compounds are disclosed in e.g. the U.S. Pat. Nos. 3,142,568 of Robert William Nottorf, issued July 28, 1964, 3,193,386 of Clayton F. A. White, issued July 6, 1965, 3,062,674 of Robert Wong, issued Nov. 6, 1962, 3,220,844 of Robert C. Houck, Donald A. Smith and Joseph S. Yudelson, issued Nov. 30, 1965. They include the water-insoluble polymers of alkyl acrylates and methacrylates, acrylic acid, sulfoalkyl acrylates or methacrylates, interpolymers of alkyl acrylates with acrylic acids, acryloyloxyalkyl sulphonic acids, acetoacetoxy alkyl acrylates such as 2-acetoacetoxyethyl methacrylate and the like. These compounds may be incorporated likewise into a separate layer of the photographic element. The vinyl polymers are generally employed in concentrations of about 20 to about 80%, most often concentrations of at least 50% by weight, based on the weight of the binding agent.

Silver halide emulsions wherein the binding agent contains a dispersed polymerized vinyl compound provide particularly good results in eliminating drag streaks and dot distortions.

The silver halide emulsions may be coated on a wide variety of supports. If desired, hydrophilic colloid layers are coated on one or both sides of the support.

Typical supports are cellulose nitrate film, cellulose ester film, polyvinyl acetal film, polystyrene film, poly(ethylene terephthalate) film, and related films or resinous materials, as well as glass, paper, metal and the like. Supports such as paper, which are coated with α-olefin polymers, particularly polymers of α-olefins containing two or more carbon atoms, as exemplified by polyethylene, polypropylene, ethylene-butene copolymers and the like may be employed likewise.

A silver halide emulsion material suitable for processing according to the present invention may be sensitized chemically according to any of the well-known techniques in emulsion making, e.g. by digesting with naturally active gelatin or various sulphur, selenium, tellurium compounds and/or gold compounds. The emulsions can be sensitized with salts of noble metals of Group VIII of the Periodic Table, which have an atomic weight higher than 100.

A silver halide emulsion material suitable for processing according to the present invention may be sensitized spectrally, e.g. ortho-sensitized or pan-sensitized conveniently with spectral sensitizing dyes. For instance, these emulsions can be sensitized spectrally by treatment with a solution of a sensitizing dye in an organic solvent. Spectral sensitizers that may be used are e.g. the cyanines, merocyanines, complex (trinuclear) cyanines, complex (trinuclear) merocyanines, styryls, and hemicyanines.

A silver halide emulsion material, which can be processed according to the present invention may also contain conventional addenda such as gelatin, plasticizers, coating aids, fog-inhibiting compounds other than said nitro compounds e.g. azaindenes, and hardeners e.g. aldehyde hardeners such as formaldehyde, mucochloric acid, glutaraldehyde bis(sodium hydrogen sulphite), maleic dialdehyde, and/or aziridines, and oxypolysaccharides.

The following comparative examples illustrates the invention.

EXAMPLE

A fine-grain gelatin silver chlorobromide lithemulsion comprising 25 mole % of bromide and 75 mole % of chloride was sensitized spectrally to green light. The emulsion was coated on a polyethylene terephthalate film support.

The resulting material was exposed to light of an incandescent lamp through a step wedge having 0.15 log exposure increments and a gray negative contact screen. The exposed material was divided in strips I, II, III, IV, V, VI, VII and VIII from which strip I was treated at 26°C in a continuously agitated tray with a fresh developer (A) having the following composition:

| | |
|---|---|
| water | 800 ml |
| hydroquinone | 15 g |
| formaldehyde bisulphite | 50 g |
| potassium metabisulphite | 4 g |
| potassium carbonate | 70 g |
| potassium bromide | 2 g |
| polyethylene glycol (average molecular weight 1500) | 0.5 g |
| boric acid | 6 g |
| water to make | 1000 ml |

The developed strips showed a dot screen wedge image.

The dot definition in the strips was evaluated after the development times indicated in the Tables A to H by comparison with standard materials, which in decreasing order to dot definition quality have the numbers 1, 2, 3, 4, 5, and 6 (1 being excellent and 6 bad).

Speed 1 = speed at density 0.30 above fog in relative log I.t values
Speed 2 = speed at density 3.00 above fog in relative log I.t values The dot quality was examined in the areas of each strip that contain 10% black and 90% white and in the areas that contain 50% black and 50% white respectively as mentioned in the following Table A.

Table A

| Development time (min) | Fog | Dot quality at 10% black | Dot quality at 50% black | Speed 1 | Speed 2 |
|---|---|---|---|---|---|
| 1 | 0.04 | 1 | 1 | 0.93 | 1.38 |
| 1½ | 0.04 | 2 | 2 | 0.59 | 0.96 |
| 2 | 0.04 | 5 | 4 | 0.39 | 0.93 |

Strip II was developed in the same way as strip I with the difference, however, of the use of a fresh developer (B) having the following composition:

| | |
|---|---|
| water | 800 ml |
| hydroquinone | 15 g |
| formaldehyde bisulphite | 50 g |
| potassium metabisulphite | 4 g |
| sodium sulphite | 6 g |
| potassium carbonate | 70 g |
| potassium bromide | 2 g |
| polyethylene glycol (average molecular weight 1500) | 0.5 g |
| boric acid | 6 g |
| water to make | 1000 ml |

The obtained results are mentioned in Table B.

Table B

| Development time (min) | Fog | Dot quality at 10% black | Dot quality at 50% black | Speed 1 | Speed 2 |
|---|---|---|---|---|---|
| 1 | 0.04 | 3 | 4 | 1.19 | 1.90 |
| 1½ | 0.04 | 2 | 3 | 0.78 | 1.36 |
| 2 | 0.04 | 4 | 2 | 0.55 | 1.02 |

Strip III was developed in the same way as strip I with the difference, however, of the use of a fresh developer (C) having the following composition:

| | |
|---|---|
| water | 800 ml |
| hydroquinone | 15 g |
| potassium metabisulphite | 4 g |
| sodium sulphite | 6 g |
| potassium carbonate | 70 g |
| potassium bromide | 2 g |
| polyethylene glycol (average molecular weight 1500) | 0.5 g |
| 5-nitro-indazole | 20 mg |
| boric acid | 6 g |
| water to make | 1000 ml |

The obtained results are mentioned in Table C.

Table C

| Development time (min) | Fog | Dot quality at 10% black | Dot quality at 50% black | Speed 1 | Speed 2 |
|---|---|---|---|---|---|
| 2 | 0.04 | 1 | 1 | 1.92 | 1.61 |
| 2½ | 0.04 | 1 | 1 | 1.73 | 1.43 |
| 3 | 0.04 | 1 | 1 | 1.64 | 1.33 |

Strip IV was developed in the same way as strip I with the difference, however, of the use of a fresh developer (D) having the following composition:

| | |
|---|---|
| water | 800 ml |
| hydroquinone | 15 g |
| formaldehyde bisulphite | 50 g |
| potassium metabisulphite | 4 g |
| sodium sulphite | 6 g |
| potassium carbonate | 70 g |
| potassium bromide | 2 g |
| 5-nitro-indazole | 20 g |
| boric acid | 6 g |
| water to make | 1000 ml |

The obtained results are mentioned in Table D.

Table D

| Development time (min) | Fog | Dot quality at 10% black | Dot quality at 50% black | Speed 1 | Speed 2 |
|---|---|---|---|---|---|
| 2 | 0.05 | 6 | 6 | 0.40 | 0.97 |
| 2½ | 0.06 | 6 | 6 | 0.38 | 0.95 |
| 3 | 0.06 | 6 | 6 | 0.37 | 0.94 |

Strip V was developed in the same way as strip I with the difference, however, of the use of a fresh developer (E) having the following composition:

| | |
|---|---|
| water | 800 ml |
| hydroquinone | 15 g |
| formaldehyde bisulphite | 50 g |
| potassium metabisulphite | 4 g |
| sodium sulphite | 6 g |
| potassium carbonate | 70 g |
| potassium bromide | 2 g |
| polyethylene glycol (average molecular weight 1500) | 0.5 g |
| 6-nitro-indazole | 20 mg |
| boric acid | 6 g |
| water to make | 1000 ml |

The obtained results are mentioned in Table E.

Table E

| Development time (min) | Fog | Dot quality at 10% black | Dot quality at 50% black | Speed 1 | Speed 2 |
|---|---|---|---|---|---|
| 2 | 0.04 | 1 | 2 | 1.21 | 1.66 |
| 2½ | 0.04 | 1 | 2 | 0.98 | 1.37 |
| 3 | 0.04 | 1 | 2 | 0.85 | 1.33 |

Strip VI was developed in the same way as strip I with the difference, however, of the use of a fresh developer (F) having the following composition:

| | |
|---|---|
| water | 800 ml |
| hydroquinone | 15 g |
| formaldehyde bisulphite | 50 g |
| potassium metabisulphite | 4 g |
| sodium sulphite | 6 g |
| potassium carbonate | 70 g |
| potassium bromide | 2 g |
| 6-nitro-indazole | 20 mg |
| boric acid | 6 g |
| water to make | 1000 ml |

The obtained results are mentioned in Table F.

Table F

| Development time (min) | Fog | Dot quality at 10% black | Dot quality at 50% black | Speed 1 | Speed 2 |
|---|---|---|---|---|---|
| 2 | 0.06 | 6 | 6 | 0.42 | 1.04 |
| 2½ | 0.07 | 6 | 6 | 0.42 | 1.00 |
| 3 | 0.07 | 6 | 6 | 0.36 | 0.88 |

Strip VII was developed in the same way as strip I with the difference, however, of the use of a first developer (G) having the following composition:

| | |
|---|---|
| water | 800 ml |
| hydroquinone | 15 g |
| formaldehyde bisulphite | 50 g |
| potassium metabisulphite | 4 g |
| sodium sulphite | 6 g |
| potassium carbonate | 70 g |
| potassium bromide | 2 g |
| polyethylene glycol (average molecular weight 1500) | 0.5 g |
| 3-methyl-5-nitro-indazole | 20 mg |
| boric acid | 6 g |
| water to make | 1000 ml |

The obtained results are mentioned in Table G.

Table G

| Development time (min) | Fog | Dot quality at 10% black | Dot quality at 50% black | Speed 1 | Speed 2 |
|---|---|---|---|---|---|
| 1 | 0.04 | 2 | 4 | 1.33 | 1.95 |
| 1½ | 0.04 | 1 | 2 | 0.95 | 1.38 |
| 2 | 0.04 | 2 | 2 | 0.66 | 1.08 |

Strip VIII was developed in the same way as strip I with the difference however of the use of a fresh developer (H) having the following composition:

| | |
|---|---|
| water | 800 ml |
| hydroquinone | 15 g |
| formaldehyde bisulphite | 50 g |
| potassium metabisulphite | 4 g |
| sodium sulphite | 6 g |
| potassium carbonate | 70 g |
| potassium bromide | 2 g |
| 3-methyl-5-nitro-indazole | 20 mg |

-continued boric acid 6 g
water to make 1000 ml

The obtained results are mentioned in Table H.

Table H

| Development time (min) | Fog | Dot quality at 10% black | Dot quality at 50% black | Speed 1 | Speed 2 |
|---|---|---|---|---|---|
| 1 | 0.05 | 6 | 6 | 0.46 | 1.17 |
| 1½ | 0.06 | 6 | 6 | 0.40 | 1.07 |
| 2 | 0.06 | 6 | 6 | 0.37 | 0.93 |

What we claim is:

1. An alkaline aqueous developer composition suited for producing halftone images showing the lith-gradation by development of silver halide recording materials in which the halide consists of at least about 50 mole % of chloride wherein said composition comprises:
   1. a p-dihydroxybenzene developing agent in an amount of about 0.05–0.50 mole per liter,
   2. a sulfite compound providing an amount of sulfite ions ($SO_3^{--}$) of at least about 5 grams per liter,
   3. a sufficient amount of an alkaline compound to impart to said composition a pH of about 9.7–11.5,
   4. a nitro-indazole corresponding to the following general formula:

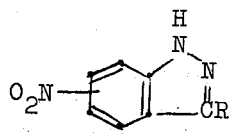

wherein:
   R is hydrogen or a lower ($C_1$–$C_5$) alkyl group, and the nitro-group is in the 5- or 6-position,
   5. a polymer containing a plurality of alkylene oxide units and having a molecular weight of at least about 1500, said polymer being present in a concentration of at least 500 mg per liter,
   6. bromide ions in a concentration of at least 0.2 g per liter, said composition containing not more than about 0.05 g/l of any auxiliary developing agent that shows a superadditive developing effect with said p-dihydroxybenzene developing agent.

2. A developer composition according to claim 1, wherein the polyoxyalkylene compound is present in the developer in an amount in the range of about 0.5 to about 2 g per liter.

3. A developer composition according to claim 1, wherein the polymeric compound containing a plurality of oxyalkylene units is a polyoxyethylene glycol with an average molecular weight of at least 1500.

4. A developer composition according to claim 1, wherein the nitro-indazole compound is 5-nitro-indazole.

5. A developer composition according to claim 1, wherein the nitro-indazole compound is present in an amount of 5 to 100 milligrams per liter.

6. A developer composition according to claim 1, wherein the composition contains formaldehyde bisulphite.

7. A developer composition according to claim 1, wherein the composition contains an onium compound.

8. A developer composition according to claim 1, wherein the composition contains 1,1'-[ethylene-tris-(oxyalkylene)]-bis-(pyridinium p-toluene-sulphonate) as onium compound.

9. A developer composition according to claim 8, wherein the onium compound is present in an amount of 0.1 to 3.0 g per liter.

10. A developer composition according to claim 1, wherein the free bromide ions are present in an amount of 0.2 to 5.0 g per liter.

11. A developer composition according to claim 1, wherein the developing agent is hydroquinone present in an amount of 0.05 mole to 0.50 mole per liter.

12. A developer composition according to claim 1, wherein the sulphite ions are present in an amount of 5 g to 100 g per liter.

13. A developer composition according to claim 1, wherein said composition contains ascorbic acid as preservative.

14. A method for developing a silver halide emulsion recording material in which the halide consists essentially of at least 50 mole % of chloride and which has been subjected to an exposure for producing an halftone print wherein the development of said material is carried out in a aqueous alkaline developing composition comprising:
   1. a p-dihydroxybenzene developing agent in an amount of about 0.05–0.50 mole per liter,
   2. a sulfite compound providing an amount of sulfite ions ($SO_3^{--}$) of at least about 5 grams per liter,
   3. a sufficient amount of an alkaline compound to impart to said composition a pH of about 9.7–11.5,
   4. a nitro-indazole corresponding to the following general formula:

wherein: R is hydrogen or a lower ($C_1$–$C_5$) alkyl group, and the nitro group is in the 5- or 6-position,
   5. a polymer containing a plurality of alkylene oxide units, said polymer being present in a concentration of at least 500 mg per liter,
   6. bromide ions in a concentration of at least 0.2 g per liter, said composition containing not more than about 0.05 g/l of any auxiliary developing agent that shows a superadditive developing effect with said p-dihydroxybenzene developing agent.

15. A method according to claim 14, wherein the exposed light-sensitive silver halide material is developed by transporting it in continuous motion through said developing composition.

* * * * *